US008382703B1

(12) United States Patent
Abdelaal

(10) Patent No.: US 8,382,703 B1
(45) Date of Patent: Feb. 26, 2013

(54) PIEZOELECTRIC DUAL-SYRINGE INSULIN PUMP

(75) Inventor: Wahied Gharieb Ali Abdelaal, Riyadh (SA)

(73) Assignee: King Saud University, Riyadh (SA)

( * ) Notice: Subject to any disclaimer, the term of this patent is extended or adjusted under 35 U.S.C. 154(b) by 22 days.

(21) Appl. No.: 13/276,135

(22) Filed: Oct. 18, 2011

(51) Int. Cl.
*A61M 31/00* (2006.01)

(52) U.S. Cl. .......................................... 604/67; 604/152

(58) Field of Classification Search .................. 604/65, 604/67, 131, 151, 152; 128/DIG. 1
See application file for complete search history.

(56) References Cited

U.S. PATENT DOCUMENTS

| | | | |
|---|---|---|---|
| 6,723,072 | B2 | 4/2004 | Flaherty et al. |
| 7,608,060 | B2 | 10/2009 | Gillespie, Jr. et al. |
| 2005/0177111 | A1 | 8/2005 | Ozeri et al. |
| 2008/0132842 | A1 | 6/2008 | Flaherty |
| 2008/0208173 | A1 | 8/2008 | Lee et al. |
| 2008/0255517 | A1 | 10/2008 | Nair et al. |
| 2009/0112155 | A1 | 4/2009 | Zhao et al. |
| 2009/0137957 | A1 | 5/2009 | Wagener |

FOREIGN PATENT DOCUMENTS

| | | |
|---|---|---|
| EP | 1513580 B1 | 3/2009 |
| WO | WO 2005074374 A2 | 8/2005 |

OTHER PUBLICATIONS

Henderson et al., "Piezoelectric motors move miniaturization forward," Electronic Products (2006), 2 pages.
Henderson, D.A., "Novel Piezo Motor Enables Positive Displacement Microfluidic Pump," (2007), 4 pages, published at www.newscaletech.com.

*Primary Examiner* — Theodore Stigell
(74) *Attorney, Agent, or Firm* — Richard C. Litman

(57) ABSTRACT

The piezoelectric dual-syringe insulin pump includes a single piezoelectric motor configured to pump insulin. The pump is controlled by a single controller. The pump uses two insulin reservoirs (in the form of two syringes), one of which is filled with a rapid-acting insulin, the other reservoir being filled with slow-acting insulin (providing the basal function). Both syringes are alternately actuated by a single PZT linear motor (particularly, a squiggle motor), depending upon polarity of the voltage applied to the motor, and feed into a common infusion line to the patient. The device includes an LCD display, audio alarm, controller, keypad, USB port, and a micro-energy harvesting circuit for recharging an on-board battery.

9 Claims, 3 Drawing Sheets

PIEZOELECTRIC DUAL-SYRINGE INSULIN PUMP

BACKGROUND OF THE INVENTION

1. Field of the Invention

The present invention relates to generally to insulin pumps, and more particularly to a piezoelectric dual-syringe insulin pump.

2. Description of the Related Art

Insulin pumps are designed to provide a controlled rate of insulin delivery to diabetic patients who would normally need multiple daily injections to regulate the blood glucose level. Some pumps, however, are subject to Radio Frequency Interference (RFI). Moreover, existing pumps may not be as accurate as required by a particular treatment protocol. These problems should be overcome by a more accurate and RFI-free pump device.

Thus, a piezoelectric dual-syringe insulin pump solving the aforementioned problems is desired.

SUMMARY OF THE INVENTION

The piezoelectric dual-syringe insulin pump includes a single piezoelectric motor configured to pump insulin. The pump is controlled by a single controller. The pump uses two insulin reservoirs (in the form of two syringes), one of which is filled with rapid-acting insulin, the other reservoir being filled with slow-acting insulin (providing the basal function). Both syringes are actuated by a single PZT (lead zirconate titanate, or Pb $[Zr_xTi_{1-x}]$ O3 where $0 \leq x \leq 1$)) linear motor (particularly, a squiggle motor), and feed into a common infusion line to the patient. The device includes an LCD (Liquid Crystal Display), audio alarm, controller, keypad, USB port and a micro-energy harvesting circuit for recharging an on-board battery.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
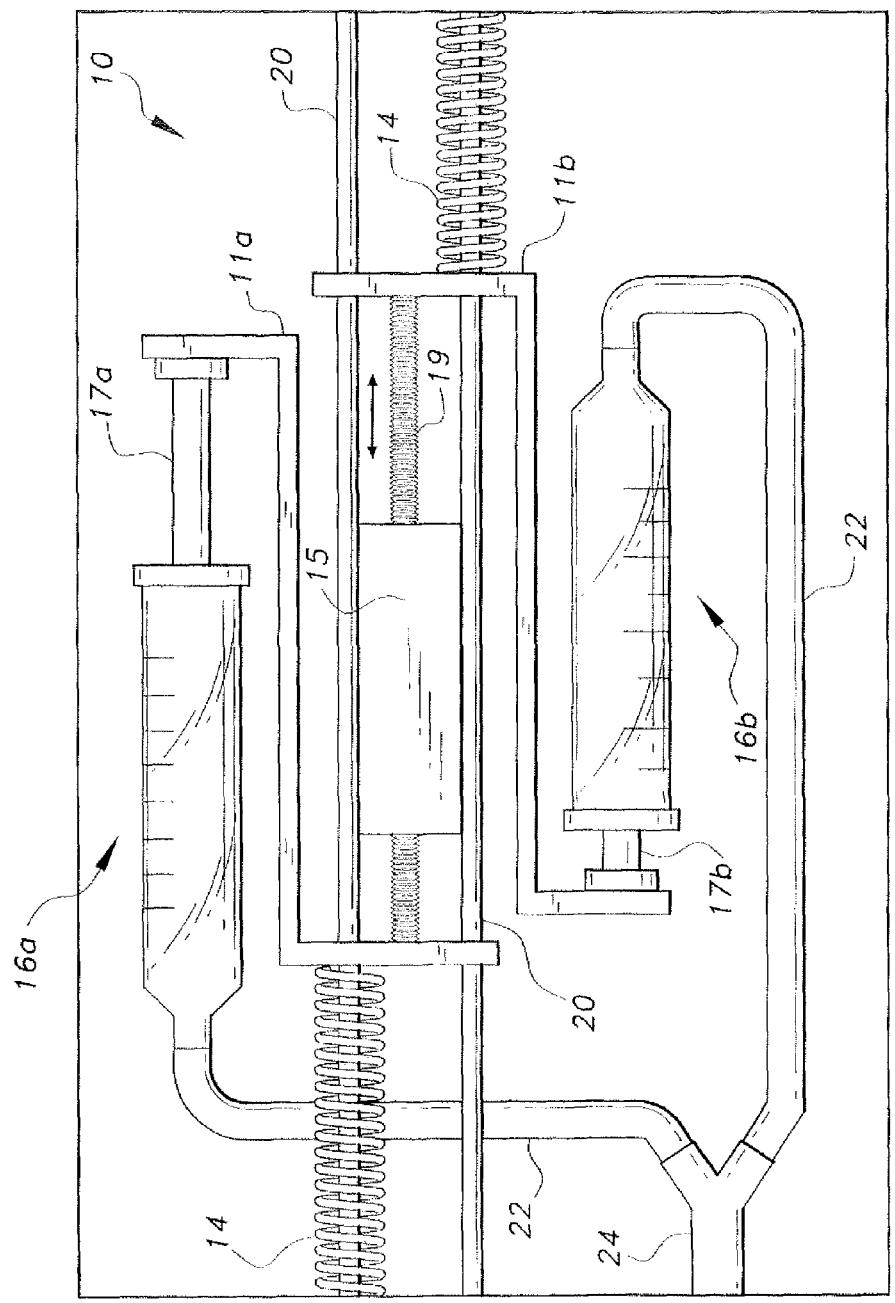
FIG. 1 is a diagrammatic plan view of a piezoelectric dual-syringe insulin pump according to the present invention.
Figure 2:
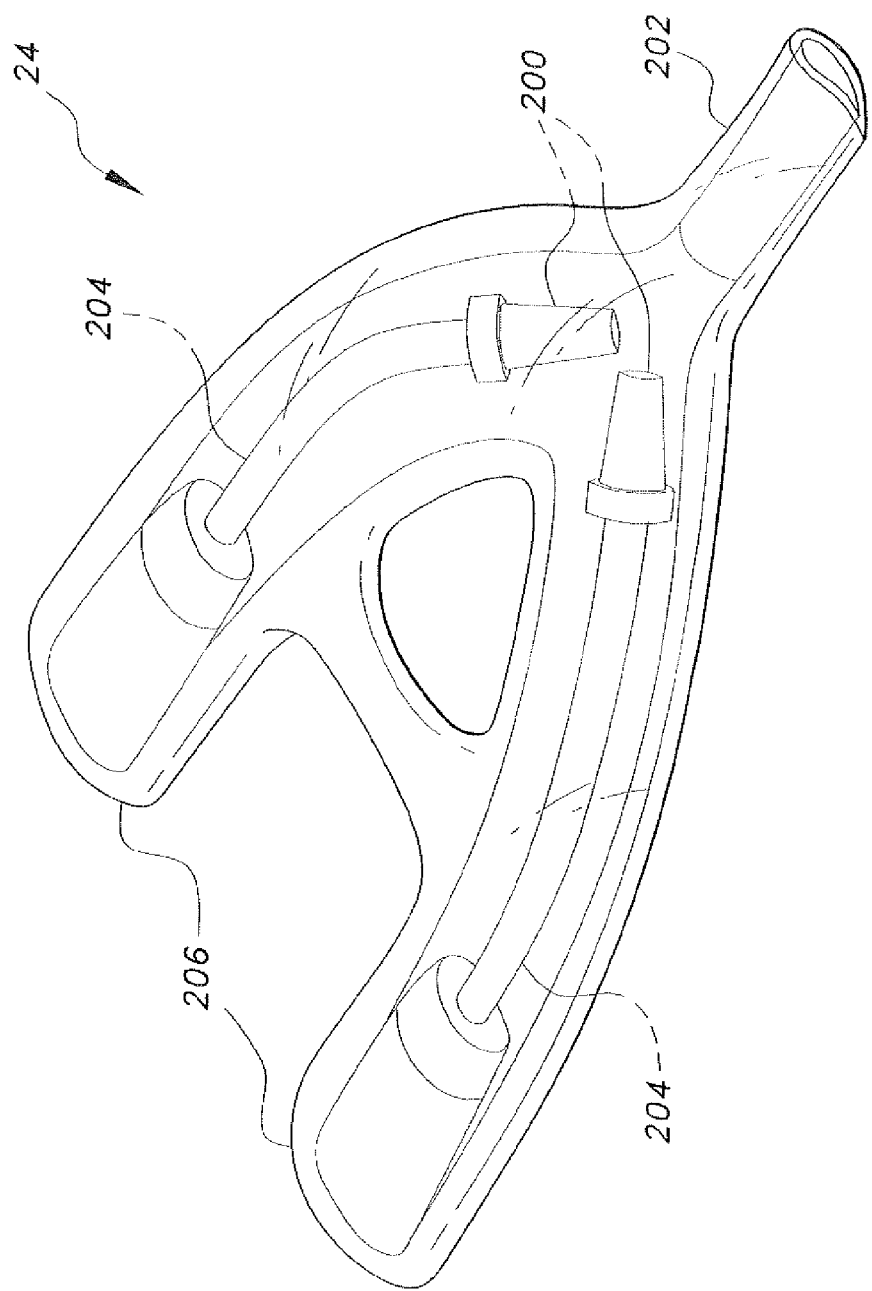
FIG. 2 is an enlarged perspective view of a dual-syringe injector used with the insulin pump of FIG. 1.
Figure 3:
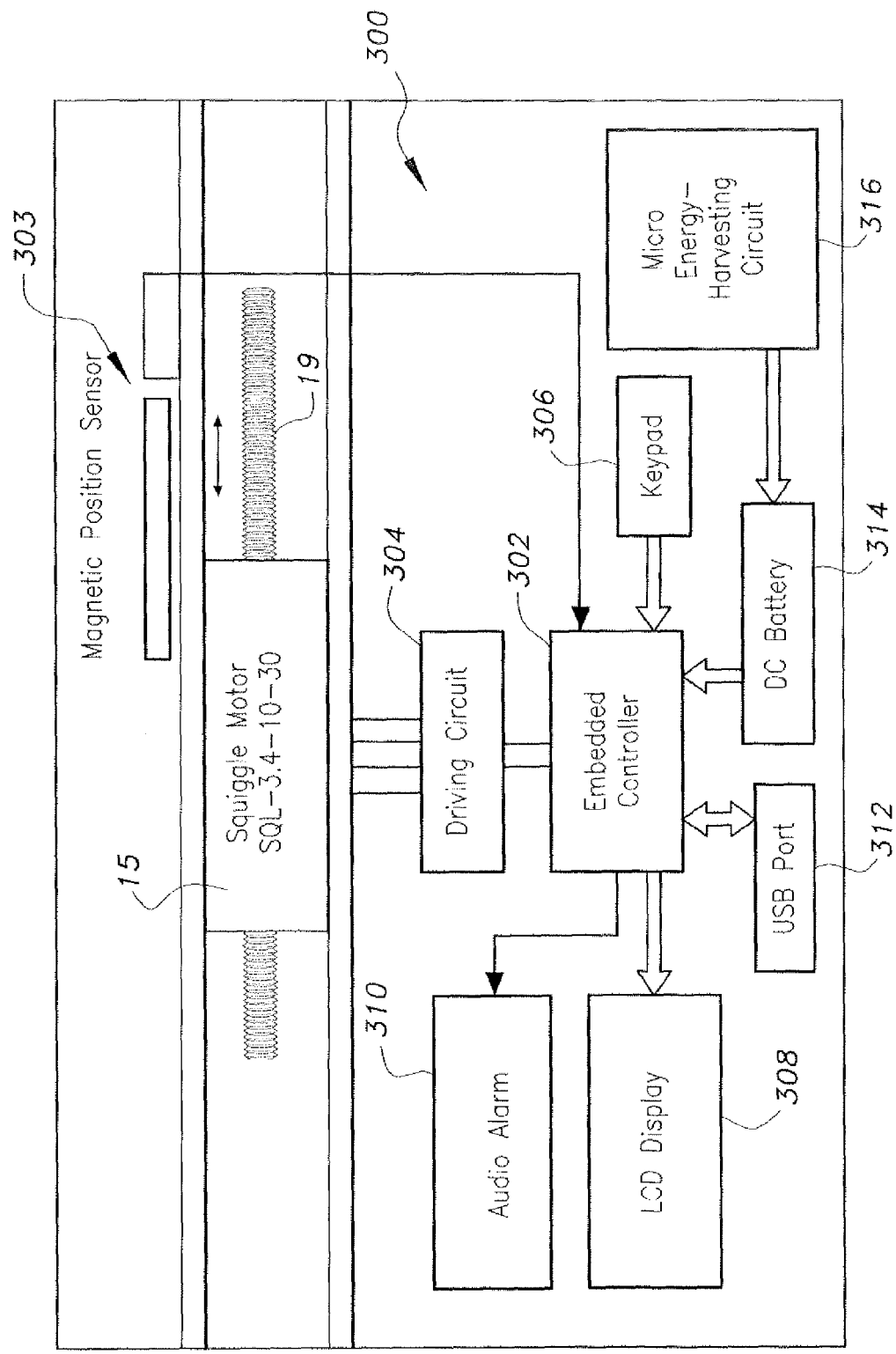
FIG. 3: is a block diagram of a control and interface circuit of the insulin pump of FIG. 1.

As shown in the FIGS. 1-3, the piezoelectric dual-syringe insulin pump 10 includes a single piezoelectric motor 15 configured to pump insulin. The pump is controlled by a single controller 302. The pump 10 uses two insulin reservoirs 16a, 16b (in the form of two syringes), one of which is filled with rapid-acting insulin, the other reservoir being filled with slow-acting insulin (providing the basal function). Both syringes 16a and 16b are actuated by a single PZT linear motor 15 (particularly, a squiggle motor). Lines or tubes 22 feed inlets 206 of a dual-syringe injector 24 (FIG. 2 shows an enlarged view of the injector 24 shown in the lower left side of FIG. 1, which feeds a common infusion line to the patient via a standard needle fitting 202 of the Y-shaped dual-syringe injector 24.

The control circuit 300 of the device includes an LCD display 308, audio alarm 310, controller 302, keypad 306, USB port 312, and a micro-energy harvesting circuit 316 for recharging an on-board battery 314. A drive circuit 304 connects the controller 302 to the linear actuator motor 15. The controller 302 is an embedded digital controller (a microcontroller or a low power FPGA chip). The LCD display 308 is preferably of the small, low power type. The small keypad 306 is provided for programming functions. The keypad 306 is used to feed the controller 302 with the required dosage settings and injection rates. The low power LCD display 308 is used to display the operating parameters and alarm conditions, if any. The audio alarm 310 is activated if abnormal conditions occur, or if the insulin syringes are empty and need to be refilled. The micro energy harvesting circuit 316 is used to extend the battery lifetime with energy from the patient's body temperature and its kinetic energy, and also a USB port 312 is added for data transfer to/from an external computer to improve the insulin therapy.

A threaded actuation member 19 is threadably disposed through the axial center of the linear motor 15 and extends from both sides of the motor 15. A magnetic position sensor 303 determines the precise position of the threaded actuation member 19, thereby allowing for precision dosing using the pump 10. The positioning of the linear motion has to be accurate; so an embedded position control loop involving the magnetic position sensor 303 is designed to compensate for the injection back pressure. In this case, the controller 302 in the closed loop calculates the required new position as a function of the required insulin dosage. The drive circuit 304 is a special circuit that generates the required ultrasonic waves for the linear ultrasonic piezoelectric motor 15. The magnetic position sensor 303 provides the feedback to the embedded controller 302. The controller 302 stores the historical position information and compares it with the required position to perform the desired programmable insulin dosage.

The pump 10 increases the capacity of the insulin pump compared to conventional pumps by using dual syringes as insulin reservoirs. The manufacturer of the motor 15, New Scale Technologies, Inc. of Victor, N.Y., has an M3 micro mechatronics module platform, which includes a SQUIGGLE° motor (Squiggle is a registered trademark of New Scale Technologies, Inc.), i.e., a revolutionary linear micromotor, a screw drive being disposed through a central axis of the motor. When energized, the motor 15 squirms in a predictable manner that threads the screw 19 linearly in a positive direction or a negative direction, depending on the polarity of the energy source to the motor.

Referring to FIG. 1, high torque/force generated in the ultrasonic motor 15 is imparted to one of the Z-shaped sliding members 11a or 11b that, in turn, slides to depress the corresponding insulin syringe plunger 17a or 17b attached thereto. Each Z-shaped member 11a, 11b has a first leg portion slidably attached to a fixed, rod-shaped, dual rail assembly 20. A second leg portion of the Z-shaped members 11a, 11b engages the syringe plungers 17a and 17b, respectively. Springs 14 are concentrically disposed around individual rails of the rail assembly 20 and provide spring bias for position return of the Z-shaped members 11b and 11a when the motor 15 changes the linear travel direction of the actuating screw 19. The axis of the motor 15 can be moved in a bidirectional way between the fixed rails 20. The rail assembly 20 is a guide for the movable Z-shaped components 11a and 11b. The motor 15 slides one of the Z-shaped members in order to drive the syringe piston and to complete the injection process. The mechanical spring 14 makes the motor axis loaded by this part if it starts to move in the reverse direction. The motor 15 works best with a preload. At any instant, only one of the syringes 16a and 16b is selected for injection according to the direction of motion.

The dual-syringe injector 24 has dual inlets 206 feeding calibrated dosing channels 204 attached to a non-return valve 200 inside each inlet direction, and routes the drug through a standard needle fitting 202 for delivery to the patient, as shown in FIG. 2. A Micro-needle is inserted in the skin of the patient's body with a minimal degree of pain.

The exemplary motor 15 used in the pump 10 is the SQUIGGLE motor developed by New Scale Technologies, Inc. This motor offers several advantages over DC motors and stepper motors, which are widely used in classical biomedical pumps for drug delivery systems. These advantages include small size and less power consumption, EMI (electromagnetic interference) resistance, speed control without the necessity of a gearbox, high force generation capability, and precision positioning control The design of the pump 10 allows for portability. The design is miniaturized, and the pump 10 is wearable and lightweight. The pump mechanism is a linear piezoelectric motor 15 due to its great advantages. Moreover, power consumption is low, both for the power motor and the electronic components. The pump 10 provides insulin solution, wherein the syringes 16a, 16b are 3 ml (300 insulin units), and this quantity is enough for 3 days. The dual-syringe can extend this period to 5-6 days. In the power supply, a low power battery 314 is used, and the drive circuit uses a step-μ, regulator to boost the low voltage. With respect to battery management, the embedded controller 302 detects low battery condition and activates the audio alarm 310, while sending a "Low battery Warning" message to the LCD display 308.

The digital electronic circuit 300 permits a user-friendly interface to tailor basal and bolus dosages to their needs. Displays/keypads, e.g., the LCD 308, are in common use, and the pump 10 uses them to provide information about insulin dosage and rates, remaining battery life, time and date, reminders, and system alarms. The embedded controller 302 includes a real-time clock so that all events can be logged and time-stamped.

With respect to electrostatic discharge, all insulin pumps must pass IEC 6 1000-4-2 electrostatic discharge (ESD) requirements. Built-in protection is used by adding ESD line protectors to exposed traces. The USB data port 312 is provided to allow data transfer to a computer and to download firmware upgrades. This allows history files to be pulled into application programs and sent to caregivers to aid in insulin therapy. The USB port 312 is used with ESD protection. The pump's use of a dual-syringe injector allows for handling of two different substances through a single needle, and consequently reduces soft tissue complications. The small size and low power consumption is achieved by using the linear piezoelectric motor 15. The system's motor 15 and one drive circuit 304 for the dual syringe is not affected by electromagnetic wave interference (EMI). No gear reduction is required for speed control. There is a high generating force due to the use of the ultrasonic piezoelectric motor. Due to the feedback loop and magnetic position sensor 303, there is very high precision positioning control for dosage and very high precise flow control for injection rates. Moreover, the micro-energy harvesting circuit 316 is added to increase the battery's lifetime.

The pump 10 can be used for drug delivery and for medical injection systems. The pump 10 is an essential integrated component in a closed-loop insulin delivery system for diabetic patients.

It is to be understood that the present invention is not limited to the embodiments described above, but encompasses any and all embodiments within the scope of the following claims.

I claim:

1. A piezoelectric dual-syringe insulin pump, comprising:
   first and second Z-shaped members;
   a dual rail assembly, the first and second Z-shaped members each having a first leg portion slidably disposed through a first rail portion and a second rail portion, respectively;
   a piezoelectric motor having a screw drive actuator, the actuator having a first end engaging the first Z-shaped member and an opposing second end engaging the second Z-shaped member;
   biasing force members indirectly applying opposing biasing forces against the opposing ends of the screw drive actuator through the Z-shaped members;
   a first syringe adapted for holding a fast-acting insulin medication, the first syringe having a first plunger, the first Z-shaped member having a second leg portion bearing against the first plunger;
   a second syringe adapted for holding a slow-acting insulin medication, the second syringe having a second plunger, the second Z-shaped member having a second leg portion bearing against the second plunger;
   a dual-syringe injector, the first and second syringes being in fluid connection with the dual-syringe injector; and
   a voltage source selectively energizing the piezoelectric motor;
   wherein when the voltage source energizes the piezoelectric motor, the motor drives the screw drive actuator member against the bias applied through the first Z-shaped member, thereby depressing the first plunger to dispense a measured dose of the fast-acting insulin medication to a patient if the voltage source is of a first polarity, or causes the motor to drive the screw drive actuator in the opposite direction to depress the second plunger to dispense a measured dose of the slow-acting insulin medication to the patient if the voltage source is of a polarity opposite the first polarity.

2. The piezoelectric dual-syringe insulin pump according to claim 1, wherein said dual-syringe injector includes:
   a needle fitting;
   non-return valves feeding the needle fitting;
   calibrated dosing channels attached to the non-return valves; and
   dual inlets feeding the calibrated dosing channels.

3. The piezoelectric dual-syringe insulin pump according to claim 1, further comprising:
   a magnetic position sensor determining precise linear position of said screw drive actuator; and
   an electronic control circuit connected to the magnetic position sensor in a feedback control loop to precisely command linear travel of said screw drive actuator for precision dose delivery to the patient.

4. The piezoelectric dual-syringe insulin pump according to claim 3, further comprising:
   a tactile input device connected to said electronic control circuit for inputting required dosage settings and injection rates to be processed by said electronic control circuit; and a low power display device connected to said electronic control circuit for selectively displaying operating parameters and alarm conditions.

5. The piezoelectric dual-syringe insulin pump according to claim 3, wherein said electronic control circuit includes a drive circuit providing ultrasonic waves actuating said piezoelectric motor.

6. The piezoelectric dual-syringe insulin pump according to claim 3, further comprising a data port connected to said electronic control circuit, the data port providing data transfer capability adapted for transferring data to and from an external computer to improve insulin therapy.

7. The piezoelectric dual-syringe insulin pump according to claim 3, further comprising a micro-energy harvesting circuit connected to said voltage source for maintaining adequate charge on said voltage source.

8. The piezoelectric dual-syringe insulin pump according to claim 3, further comprising an audio alarm connected to said electronic control circuit, the audio alarm audibly indicating alarm conditions detected by said electronic control circuit.

9. The piezoelectric dual-syringe insulin pump according to claim 1, wherein said piezoelectric motor comprises a PZT motor.

* * * * *